(12) United States Patent
Waugh et al.

(10) Patent No.: US 8,580,317 B2
(45) Date of Patent: Nov. 12, 2013

(54) COMPOSITIONS AND METHODS FOR TREATING ACNE

(75) Inventors: Jacob M. Waugh, Mountain View, CA (US); Jae Hoon Lee, Union City, CA (US)

(73) Assignee: Revance Therapeutics, Inc., Newark, CA (US)

( * ) Notice: Subject to any disclaimer, the term of this patent is extended or adjusted under 35 U.S.C. 154(b) by 902 days.

(21) Appl. No.: 11/816,670

(22) PCT Filed: Mar. 30, 2006

(86) PCT No.: PCT/US2006/012095
§ 371 (c)(1),
(2), (4) Date: Jul. 1, 2009

(87) PCT Pub. No.: WO2006/105450
PCT Pub. Date: Oct. 5, 2006

(65) Prior Publication Data
US 2010/0021571 A1    Jan. 28, 2010

Related U.S. Application Data

(60) Provisional application No. 60/666,531, filed on Mar. 30, 2005.

(51) Int. Cl.
*A61K 36/00* (2006.01)
*A61K 36/60* (2006.01)
*A61K 36/236* (2006.01)
*A61K 36/539* (2006.01)
*A61K 36/14* (2006.01)
*A61K 36/28* (2006.01)
*A61K 36/534* (2006.01)

(52) U.S. Cl.
USPC .......... 424/725; 424/757; 424/770; 424/747; 424/764; 514/859

(58) Field of Classification Search
None
See application file for complete search history.

(56) References Cited

U.S. PATENT DOCUMENTS

| | | | |
|---|---|---|---|
| 4,800,197 A | 1/1989 | Kowcz et al. | |
| 4,923,900 A | 5/1990 | De Villez | |
| 5,470,323 A * | 11/1995 | Smith et al. | 604/289 |
| 5,470,884 A | 11/1995 | Corless et al. | |
| 5,753,637 A * | 5/1998 | Fried | 514/161 |
| 5,869,062 A | 2/1999 | Oliver | |
| 5,910,312 A | 6/1999 | Fried | |
| 5,958,436 A | 9/1999 | Hahn et al. | |
| 2003/0069148 A1 | 4/2003 | Booker et al. | |
| 2003/0175328 A1 | 9/2003 | Shefer et al. | |
| 2004/0156873 A1* | 8/2004 | Gupta | 424/401 |
| 2004/0185022 A1 | 9/2004 | Rubin | |
| 2004/0242588 A1 | 12/2004 | Dejovin | |
| 2005/0165079 A1* | 7/2005 | Shanler et al. | 514/401 |

FOREIGN PATENT DOCUMENTS

| | | |
|---|---|---|
| BE | 903 646 | 5/1986 |
| JP | 2002-037736 | 2/2002 |
| JP | 2002-138033 | 5/2002 |
| JP | 2002-542178 | 12/2002 |
| JP | 2004-196828 | 7/2004 |
| JP | 2004-269494 | 9/2004 |
| WO | WO 93/21899 | 11/1993 |
| WO | WO 95/31978 | 11/1995 |
| WO | WO 03/028740 | 4/2003 |
| WO | WO 03/049769 | 6/2003 |
| WO | WO 2004/073720 | 9/2004 |
| WO | WO 2004/091595 | 10/2004 |
| WO | WO 2004/098616 | 11/2004 |

OTHER PUBLICATIONS

Nonfinal Rejection dated Nov. 15, 2007 in corresponding U.S. Appl. No. 11/278,105.
Final Office Action dated Aug. 18, 2008 in corresponding U.S. Appl. No. 11/278,105.

* cited by examiner

*Primary Examiner* — Qiuwen Mi
(74) *Attorney, Agent, or Firm* — Kenneth H. Sonnenfeld; Joseph D. Eng, Jr.; King & Spalding LLP

(57) ABSTRACT

This invention provides anti-acne kits that are useful for treating acne, especially severe cases of acne. The anti-acne kits include a vasoconstrictor and an anti-acne agent, and optionally one or more of a a skin lightening therapeutic, a sealing layer, a skin cleanser, an astringent, a skin penetration enhancer, a sunscreen, and nutritional supplements that promote healing of acne lesions. This invention also provides methods for treating acne using a vasoconstrictor in conjunction with an anti-acne agent.

9 Claims, No Drawings

COMPOSITIONS AND METHODS FOR TREATING ACNE

BACKGROUND OF THE INVENTION

Acne is a disease of the sebaceous hair follicles, often called pores. At the base of each hair follicle is a gland called the sebaceous gland, which produces sebum. Sebum is an oily substance that keeps the skin moist and pliable, which under normal circumstances travels along the hair follicle to the surface of the skin. A blemish begins approximately 2-3 weeks before it appears on the skin's surface. As the skin renews itself, the old cells die and slough off. When cells are shed unevenly and clump together with the sebum it forms a plug. Sebum which normally drains to the surface gets blocked and bacteria begin to grow. The rapid growth of the bacteria in combination with the accumulated sebum cause the follicle to enlarge and result in a mild form of acne called comedones, which are non-inflammatory. Both whiteheads and blackheads start out as a "microcomedone" and then become skin blemishes called comedones, either a whitehead or a blackhead. Acne is trapped sebum and bacteria (*propionibacterium acnes*) growing in a plugged follicle. Sebaceous glands are most numerous on the face, chest, back, neck and scalp; consequently, these are the most common sites of acne. The most common factors that cause acne are hormones, increased sebum production, bacteria (*Propionibacterium Acnes*), and changes inside of the hair follicle. Acne may progress to an inflammatory type of acne lesions that are red in color called papules, pustules and nodules.

There are many types of acne, ranging in severity from mild to severely disfiguring. Acne vulgaris is the most common form of acne which includes several types of pimples. These acne lesions include blackheads, whiteheads, papules, pustules, nodules and cysts.

Mild to moderate acne vulgaris is characterized by whiteheads, blackheads, papules, and pustules. A whitehead is formed when a pore is completely blocked, trapping sebum, bacteria, and dead skin cells below the skin surface causing a white appearance on the surface. Whiteheads are normally quicker in life cycle than blackheads. A blackhead is formed when a pore is only partially blocked, allowing some of the trapped sebum, bacteria, and dead skin cells to drain to the surface slowly. The black color is due to a reaction of the skin's own pigment, melanin, reacting with the oxygen in the air. A blackhead tends to be a stable structure. Blackheads can often take a long time to clear because the contents very slowly drain to the surface. Papules are small, red, tender bumps with no head. Papules are the earliest stage in the development of what are normally considered the typical "pimple". Papules are an intermediate in the progression of acne between the non-inflammatory and inflammatory stages. Pustules are similar to whiteheads, but are inflamed, and appear as a red circle with a white or yellow center.

Severe acne vulgaris is characterized by nodules and cysts. Nodular acne consists of acne spots which are much larger, can be quite painful, and can sometimes last for months. Nodules are large, hard bumps under the skin's surface. Scarring is common with nodules. An acne cyst can appear similar to a nodule, but is pus-filled, and can been described as having a diameter of 5 mm or more across. They can be painful and scarring is common with cystic acne.

Acne rosacea can look similar to the aforementioned acne vulgaris, and the two types of acne are sometimes confused for one another. Rosacea affects millions of people, most of whom are over the age of 30. It appears as a red rash which is normally confined to the cheeks, nose, forehead and chin. The redness is often accompanied by bumps, pimples, and skin blemishes. Blood vessels may also become more visible on the skin. Blackheads are not a part of rosacea. It is more prevalent in women, but often more severe when found in men. Left untreated, it can cause swelling of the nose and the growth of excess tissue, a condition called rhinophyma.

Acne conglobata is the most severe form of acne vulgaris and is more common in males. It is characterized by numerous large lesions, which are sometimes interconnected, along with widespread blackheads. It can cause severe, irrevocable damage to the skin, and disfiguring scarring. It is found on the face, chest, back, buttocks, upper arms, and thighs. The age of onset for acne conglobata is usually between 18 and 30 years, and the condition can stay active for many years.

Acne fulminans is an abrupt onset of acne conglobata which normally afflicts young men. Symptoms of severe nodulocystic, often ulcerating acne are apparent. As with acne conglobata, extreme, disfiguring scarring is common. Acne fulminans is unique in that it also includes a fever and aching of the joints.

Gram-negative folliculitis is a bacterial infection characterized by pustules and cysts, possibly occurring as a complication resulting from a long term antibiotic treatment of acne vulgaris. It is a rare condition, and prevalence in males versus females is unknown.

Pyoderma Faciale is severe facial acne affects only females, usually between the ages of 20 to 40 years old, and is characterized by painful large nodules, pustules and sores which may leave scarring. It begins abruptly, and may occur on the skin of a woman who has never had acne before. It is confined to the face, and usually does not last longer than one year, but can wreak havoc in a very short time.

Teenage (adolescent) acne: Most cases of acne that require treatment occur in individuals 9 to 19 years of age. Boys and girls are equally affected but the condition is usually more severe in boys. No ethnic groups are predisposed to acne, but certain cosmetic practices, such as the use of oily grooming agents, can lead to a specific pattern of lesions. Internal factors that may cause adolescents acne include endogenous hormones (androgens, progesterone) and specific drugs (oral contraceptives, isoniazid, phenytoin, corticosteroids, lithium-containing compounds). External factors include skin bacteria, especially *Propionibacterium acnes*; industrial chemicals (petroleum, animal and vegetable oils); oil- or wax-containing cosmetics; greasy sunscreen or suntan preparations; and local pressure from objects such as headbands, shoulder pads, or helmets. Excessive perspiration and emotional stress can also aggravate acne. Androgens (e.g., testosterone) will increase the size of sebaceous glands and, in people prone to acne, increase the production of sebum. In women, fluctuations in estrogen during the menstrual cycle change the sensitivity of sebaceous glands to androgens. During puberty, the skin cells lining the follicle shed more quickly, mix with the increased levels of sebum and increase the likelihood of the pores becoming clogged.

Adult acne: Twenty percent (20%) of the adult population is afflicted by adult acne, most of them women. Modern-day job related stress, pollution, poor nutrition and bad cosmetics are among the major contributing factors. A common case of adult acne consists of blackheads and whiteheads, while others developed inflamed acne papules or pustules.

Approximately 85% of people worldwide suffer from acne at some point in their lives, leading to more than 103 million affected by acne at any given moment. Approximately 17 million people in the U.S. have acne resulting in approximately 5.5 million visits to the physicians each year.

Acne vulgaris occurs in up to 95% of the population in westernized societies; acne vulgaris is a nearly universal skin disease afflicting 79% to 95% of the adolescent population. In men and women older than 25 years, 40% to 54% have some degree of facial acne, and clinical facial acne persists into middle age in 12% of women and 3% of men. (Cordain L, Lindeberg S, Hurtado M, Hill K, Eaton S B, Brand-Miller J. Acne vulgaris: a disease of Western civilization. Arch Dermatol 2002 December; 138(12):1584-90).

Current medications include a variety of topical and systemic medications such as antibiotics, anti-infectives, anti-inflammatories, hormone therapies, keratolytics, and retinoids. The over the counter medication include benzoyl peroxide, salicylic acid, sulfur, and resorcinol.

Benzoyl peroxide medication is very effective for killing acne-causing bacteria. Benzoyl peroxide first saw use in the 1930's, and remains a mainstay of acne treatment because it has proven itself to work well. To this day, benzoyl peroxide actually kills *propionibacterium acnes* (*P. Acnes*) better than any other medication on the market, prescription or otherwise. Benzoyl peroxide is available in non-prescription concentrations of 2.5%, 5% and 10%.

Many anti-acne agents, including benzoyl peroxide, have a high flux into the skin. While this penetration is advantageous during the initial application, the rapid subsequent diffusion in the skin means that the anti-acne agent will diffuse away from the acne lesion to be treated (a phenomenon known as "outflow"). In turn, this means that the efficacy of the anti-acne agent is lessened, because of the relatively short dwell time of the anti-acne agent in the area of the acne lesion. Thus, it would be advantageous to have a method and a kit that would decrease the outflow of the anti-acne agent from the area of the acne lesion.

SUMMARY OF THE INVENTION

This invention provides methods and kits for treating acne, especially severe cases of acne. The invention involves using a vasoconstricting agent in conjunction with an anti-acne agent to treat acne lesions. In preferred embodiments, the vasoconstricting agent is applied prior to the anti-acne agent, and serves to reduce the outflow of anti-acne agent from the treated acne lesion. The vasoconstricting agent also simultaneously decreases the redness and swelling of the acne lesion. Thus, the vasoconstricting agent helps to conceal the acne lesion, while also helping to maintain a higher concentration of anti-acne agent in the area of the acne lesion. This, in turn, promotes healing and helps to prevent further acne outbreaks.

In addition to a vasoconstricting agent and an anti-acne agent, the kits of this invention may include components that promote the healing of existing acne lesions and/or help to conceal the acne lesions.

Accordingly, one object of this invention is to provide a kit for the treatment of acne. The kit includes a vasoconstrictor and an anti-acne agent, and optionally a skin lightening therapeutic and/or a sealing layer.

Another object of this invention is to provide a method for the treatment of acne. The method includes applying a vasoconstrictor, following by an anti-acne agent. If desired, a skin-lightening therapeutic and/or a sealing layer may be applied as well.

DETAILED DESCRIPTION OF THE INVENTION

This invention treats acne, including severe cases of acne, by enhancing the efficacy of topical anti-acne agents. The invention involves applying a vasoconstricting agent to the acne lesion, usually prior to the application of the anti-acne agent. Without wishing to be bound by any particular scientific theory, it is believed that the enhanced efficacy of a topical anti-acne agent that is observed when used in conjunction with a vasoconstrictor results from reduced outflow of the anti-acne agent from an acne lesion. Thus, the local dermal dwell time of the anti-acne agent is increased relative to the situation where no vasoconstrictor is applied, so that a greater anti-acne effect is observed for a given dosage of anti-acne agent. The vasoconstrictor also has the beneficial effect of reducing the redness and swelling of the acne lesion (usually within minutes after application), so as to help conceal the acne lesion.

Accordingly, this invention provides an anti-acne kit for treating acne. The anti-acne kit includes at least a vasoconstrictor and an anti-acne agent. The anti-acne kit may optionally contain a skin-lightening therapeutic to help conceal the acne lesion and/or a sealing layer to minimize evaporation and provide some degree of occlusion. Other components that may be a part of the kit include compositions or patches that act as sealing layers, skin cleansers, skin penetration enhancers, and nutritional supplements. Different anti-acne kits can be tailored for spot treatment versus more diffuse treatment, for different skin types, and for night versus day treatment. The anti-acne kits according to the invention can additionally be included as a part of a larger kit or skin care regimen that includes tailored cleansers, toners, balancers, moisturizers and/or various cosmetic or therapeutic topicals.

Vasoconstrictors

The vasoconstrictors contemplated by the invention are not particularly limited and include any compound that has vasoconstricting properties and the ability to penetrate the skin. In preferred embodiments, the inherent chemical properties of the vasoconstrictor allow it to penetrate the skin easily. However, this invention also contemplates modulating the ability of a vasoconstrictor to penetrate the skin by combining the vasoconstrictor with other components. For example, the skin penetration ability of a vasoconstrictor with normally low transdermal flux may be increased through the use of skin penetration agents, as disclosed herein. On the other hand, if desired, the skin penetration ability of the vasoconstrictor may be intentionally decreased. For example, a vasoconstrictor may be mixed with an appropriate emulsion that has the effect of slowing the penetration of the vasoconstrictor.

Non-limiting examples of the vasoconstricting agents contemplated by the invention include tetrahydrozoline HCl 0.05%, naphazoline HCl 0.03%, oxymetazoline HCl 0.025%, guava extract, ellagic acid, caffeine, cypress oil, *hamamelis* (witch hazel), peppermint extract, chamomile oil, and bugleweed. Generally, vasoconstrictors according to this invention may be dissolved in an appropriate pharmaceutically or cosmetically acceptable solvent and applied directly to the skin. However, in preferred embodiments, the vasoconstrictors are combined with a cream or gel base, so that application of the vasoconstrictor is more easily localized and controlled. Any pharmaceutically or cosmetically acceptable gel or cream bases may be used. Suitable gels include, for example, cellulose-based gels, (e.g., hydroxyethyl cellulose (HEC), hydroxypropyl cellulose (HPC), and carboxymethyl cellulose (CMC)) and acrylate copolymers. Suitable cream bases include emulsions formed from a water phase of a humectant, a viscosity stabilizer and water, an oil phase of fatty acid alcohol, a semi-solid petroleum hydrocarbon and an emulsifying agent and a phase containing the vasoconstrictor of the invention dispersed in an aqueous stabilizer-buffer solution. If desired, stabilizers may be added. Any conventional stabilizer can be utilized in accordance with this invention. Cream-base pharmaceutical formulations containing the vasoconstrictor may be composed of, for example, aqueous emulsions containing a fatty acid alcohol, semi-solid petroleum hydrocarbon, 1,2-ethyleneglycol and an emulsifying agent.

While the vasoconstrictor itself aids in reducing the swelling and redness associated with an acne lesion, the invention also provides for skin-lightening therapeutics to decrease the appearance of redness and discoloration further. These skin-lightening therapeutics enhance the cosmetic concealing effect of the vasoconstrictor and typically are applied after the vasoconstrictor, although concurrent application with the vasoconstrictor is also contemplated by the invention. By way of example only, the skin lightening therapeutic may be albatin, arbutin, bearberry extract, mulberry extract, licorice extract, skull cap, azelaic, ascorbyl glucosamine, magnesium ascorbyl phosphate, ascorbic acid, coltsfoot extract, gallic acid, nutmeg, ramulus mori extract or kojic acid.

Anti-Acne Agents

The anti-acne kits according to this invention also include a topical anti-acne agent. As used herein, an anti-acne agent is any compound with antibacterial and/or anti-inflammatory properties that kills the bacteria associated with acne and/or reduces the inflammation of the acne lesion. Non-limiting examples of suitable anti-acne agents include benzoyl peroxide, salicylic acid, glucose oxidase, magnesium hydroxide, lactoperoxidase, pyridoxine hydrochloride, magnesium gluconate, usnic acid, and triclosan. This invention, however, also contemplates using anti-acne agents derived from herbal extracts. Examples of suitable herbal extracts include, but are not limited to *eupatorium ayapana* extract, *fumaria officinalis* extract, oak root extract, spikenard, *spilanthes acmella* extract, szechuan pepper, *echium lycopsis* extract, lemongrass extract, oregano, *orobanche cernua* extract, *terminalia sericea, alkanna tinctoria* extract, anise, barberry, *calendula* extract, *centella asiatica*, chitosan, coriander, *echinacea, eucalyptus* extract, farnesol, gentian violet extract, goldenseal, grape seed extract, hoelen, hops, hyssop, labdanum oil, lactoferrin, *lentinus edodes* extract, manuka oil, *melaleuca cajeputi* oil, myrrh, niaouli oil, *parietaria officinalis* extract, pine cone extract, *ranunculus ficaria* extract, red raspberry extract, sea whip extract, soapwort, sulfur, *thuja occidentalis* extract, vetiver oil or extract, *ganoderma lucidum* extract, witch hazel, melilot, cucumber extract, *aloe vera, aloe* extract, areca nut extract, green tea extract, grapefruit seed extract, black cumin, garlic oil or extract, lavender extract, lemon peel extract, walnut extract, *arnica* extract, *angelica* root extract, bayberry extract, *echinacea, quassia* extract, sage oil and extract, thyme oil and extract, rosemary extract, ivy extract, sage extract, sandalwood extract, nettle extract, bearberry extract, and licorice extract.

In preferred embodiments, the anti-acne agent is applied following the application of the vasoconstrictor. This sequence is used in order to prevent the outflow of the anti-acne agent from the area of the acne lesion. In some cases, the anti-acne agent is applied immediately after the application of the vasoconstrictor. However, in other cases, there is a delay period between the application of the vasoconstrictor and the anti-acne agent. Examples of suitable delay time includes anywhere from 15 seconds to 30 minutes, more preferably between 45 seconds and 15 minutes, and even more preferably between one minute and five minutes. Note, however, that the invention is not restricted to sequential application of the vasoconstrictor and the anti-acne agent. This invention also contemplates concurrent application of the vasoconstrictor and the anti-acne agent. An example where this embodiment is useful is when the user does not have time to perform multiple steps, and/or the outflow of the anti-acne agent is not significant on the timescale that the vasoconstrictor takes effect.

Sealing Layers

Certain embodiments of this invention provide for a topical sealing layer after application of the anti-acne agent. This optional sealing layer is used to seal the treated area and/or to occlude it in order to improve tissue levels. For example, the sealing layer may be a temporary occlusive barrier that acts as a temporary patch for night treatment. The patch may contain, for example, silicone, polytetrafluoroethylene (PTFE), polyethylene glycol (PEG), hydroxypropyl cellulose (HPC), petrolatum, or acrylate copolymer.

Alternatively, the sealing layer may be a topically applied emulsion that creates a protective barrier while providing a cosmetic effect (for daytime treatment for example). A cosmetic effect may be achieved, for example, if the emulsion includes an agent capable of diffracting, refracting, or reflecting light (such as mica) and/or if the emulsion is tinted to match the color of unblemished skin. The cosmetic effect is beneficial because it remains even after the effect of the vasoconstrictor has abated.

Skin Cleanser

In certain embodiments of the invention, a skin cleanser is used prior to the application of the vasoconstrictor. The skin cleanser is used to reduce pro-acne factors, including excess oil, bacteria, and dead skin that may clog pores.

Suitable skin cleansers are not particularly limited, and may be any cosmetically acceptable cleanser. For example, the skin cleanser can contain any anionic surfactant having a hydrophobic moiety, such as a carbon chain having about 8 to about 30 carbon atoms, and more preferably about 12 to about 20 carbon atoms, and further having a hydrophilic moiety, such as sulfate, sulfonate, carbonate, phosphate, or carboxylate. The hydrophobic carbon chain may also be etherified, such as with ethylene oxide or propylene oxide, to impart a particular physical property, such as increased water solubility or reduced surface tension to the anionic surfactant.

Non-limiting examples of suitable anionic surfactants include allyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, McCutcheon Division, MC Publishing Co., Glen Rock; N.J., pp. 263-266, incorporated herein by reference. Numerous other anionic surfactants, and classes of anionic surfactants, are disclosed in Laughlin et al. U.S. Pat. No. 3,929,678, which is hereby incorporated herein by reference.

Appropriate anionic surfactants include a $C_8$-$C_{18}$ alkyl sulfate, a $C_8$-$C_{18}$ fatty acid salt, an ethoxylated $C_8$-$C_{18}$ alkyl ether sulfate, a $C_8$-$C_{18}$ alkamine oxide, a $C_8$-$C_{18}$ alkyl sarcosinate, a $C_8$-$C_{18}$ sulfoacetate, a $C_8$-$C_{18}$ sulfo succinate, a $C_8$-$C_{18}$ alkyl diphenyl oxide disulfonate, a $C_8$-$C_{18}$ alkyl carboxylate, a $C_8$-$C_{18}$ alpha-olefin sulfonate, a methyl ester sulfonate, and mixtures thereof. The $C_8$-$C_{18}$ alkyl group may be straight chain (e.g., lauryl) or branched (e.g., 2-ethylhexyl). The cation of the anionic surfactant can be an alkali metal (preferably sodium or potassium), ammonium, $C_1$-$C_4$ alkylammonium (mono-, di-, tri), or $C_1$-$C_3$ alkanolammonium (mono-, di-, and tri-).

Non-limiting examples of surfactants that are appropriate for the skin cleanser of this invention include lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates, myristyl sulfates, oleates, stearates, tallates, cocamine oxide, decylamine oxide, myristamine oxide, ricinoleates, cetyl sulfates, and similar anionic surfactants.

The skin cleansers contemplated by this invention may also be combined with exfoliating agents, in order to help reduce the blockage of skin pores. Examples of suitable exfoliating agents include fine silica particles and polymer microparticles.

Skin Penetration Enhancers

In certain embodiments of the invention, the area of skin containing the acne lesion is treated with a penetration enhancer during or immediately after the cleansing step in order to enhance the penetration of the subsequently applied vasoconstrictor. Suitable skin penetration enhancers include, for example, surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one; alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; organic acids, particularly salicylic acid and salicylates, citric acid and succinic acid.

Orally Administered Nutritional Supplements

This invention also contemplates using orally administered nutritional supplements in conjunction with the anti-acne agents disclosed herein. For example, the nutritional supplements may be in the form of a multivitamin tablet or capsule that contains vitamins and minerals known to promote wound healing. In particularly preferred embodiments, such vitamins and minerals are selected from the group consisting of vitamin A, B-vitamins, vitamin C, vitamin E, and zinc. The specific form of the vitamin or mineral is not limited, provided that it is pharmaceutically acceptable. For example, vitamin A may be administered as vitamin A palmitate or as beta-carotene. As another example, zinc may be administered as zinc ascorbate or zinc amino acid chelate.

Other, non-vitamin supplements that are beneficial for wound healing are also contemplated by the invention. Such non-vitamin supplements include, for example, ornithine alpha-ketoglutarate (OKG), glucosamine sulfate, chondroitin sulfate, *aloe vera, gotu kola* extract, and echinacea.

Astringents

In certain embodiments of the invention, an astringent is used to provide skin tightening or toning effect or to help reduce sebum production or cleanse skin. In most cases, the astringent is applied before the vasoconstrictor. The astringent may be used in conjunction with, or in lieu of, the skin cleansers as described herein. Non-limiting examples of astringents include zinc oxide, zinc sulfate, *calendula* extract, *sambucus* extract, sandalwood extract, oak bark extract, white lily extract, arnica extract, plantain extract, St. John's wort extract, yarrow extract, sage extract, passion fruit extract, walnut extract, chamomile extract, cucumber extract, mulberry glycolic extract, gentian root extract, lemon extract, rose bud extract, with hazel extract, comfrey extract, geranium extract, mint extract, rosemary extract, myrrh extract, apple extract, bayberry extract, bilberry extract, clary sage extract, cornflower extract, cranesbill extract, hawthorn extract, horse chestnut extract, raspberry concentrate, red raspberry extract, rose oil and extract, horsetail extract, ivy extract, birch bark extract, watercress extract, alfalfa extract, bay oil, cabbage rose, citrus extract, dandelion extract, goldenseal extract, hops extract, orange extract, tea tree oil, aqleppo gall, areca nut extract, yarrow extract, elecampane, nettle extract, eyebright extract, juniper oil, tamarind, kola extract, lemongrass oil, rhubarb extract, olive leaf extract, sorrel extract, sumac extract.

Analgesic Agents

In certain embodiments of the invention, an analgesic agent is used to alleviate pain associated with acne lesions The analgesic agent may be a separate component of the kits of this invention, or it may be combined with other components. In some embodiments, the analgesic agent is combined with the vasoconstrictor to provide pain relief at the early stages of the acne treatment. In other cases, however, the analgesic agent is applied as a part of the sealing layer. Non-limiting examples of analgesic agents include Indian olibanum, thorn apple extract, kava-kava extract, *Irvingia gabonensis* kernel extract, *Portulaca Oleracea* extract, poppy seeds, peppermint extract, tree tea oil, *Cannabis sativa* (hemp) extract, *Papaver somniferum* extract, *Capsicum* extract, and *Salix* (willobark) extract, clover leaf extract, Coriander leaf extract, lemon balm extract, and rhizome (ginger root) extract.

Sunscreen Agents

In certain embodiments of the invention, sunscreen agents are used to protect skin from the sun by absorbing or blocking harmful ultraviolet radiation or to help reduce damages from prolong sun exposure or to prevent sunburns. Furthermore, sunscreen agents can be combined with anti-inflammatory agents such as aloe vera and cucumber. Generally, the sunscreen agents are applied after the anti-acne agent, although this sequence is not limiting. Examples of sunscreen agents contemplated by the invention include, but are not limited to, PABA, benzophenone, avobenzone, homosalate, octinoxate, octisalate, oxybenzone, titanium dioxide, aminobenzoic acid, padimate, octocrylene, octyl salicylate, octyl methoxycinnamate, dioxybenzone, menthyl anthranilate, lisadimate, phenylbenzimidazole, sulisobenzone, zinc oxide, trolamine salicylate, roxadimate, bumetrizole, octocrylene, Tinosorb S, Tinosorb M, azelaic acid, vitamin C, kinetin, horse chestnut bark extract, aleppo gall, shea butter, kukui nut oil, everlasting oil, aesculin, kojic acid, karite butter, titanium oxide, magnesium silicate, kalin, ferric oxide, red petrolatum, and magnesium oxide.

EXAMPLES

Example 1

Two-Step Acne Treatment

This example provides a two step treatment for acne. The first step involves topically applying a vasoconstricting composition to the acne lesion to be treated. Suitable vasoconstricting compositions include tetrahydrozoline HCl 0.05%, naphazoline HCl 0.03%, or oxymetazoline HCl 0.025% in an aqueous base containing HPC to increase the viscosity for ease of application. Upon application of the vasoconstricting composition, the redness and swelling of the acne lesion diminishes, making the acne lesion less noticeable. After about 5 minutes, a second step is performed which involves topically applying 5% benzoyl peroxide 5% in an oil-in water moisturizer base. In this example, the benzoyl peroxide 5% is tinted to match the skin tone of the user, but this tinting is optional. Within two days, the acne lesion has healed substantially.

Example 2

Three-Step Acne Treatment for Nighttime Use

This example provides a three-step nighttime treatment for acne. The first step involves topically applying a vasoconstricting composition to the acne lesion to be treated. Suitable vasoconstricting compositions include tetrahydrozoline HCl 0.05%, naphazoline HCl 0.03%, or oxymetazoline HCl 0.025% in an aqueous base containing HPC to increase the viscosity for ease of application. Upon application of the vasoconstricting composition, the redness and swelling of the acne lesion diminishes, making the acne lesion less noticeable. After about 5 minutes, a second step is performed which involves topically applying 5% benzoyl peroxide in an oil-in water moisturizer base. The acne lesion is then covered with a patch that includes silicone on the skin-side of the patch. The patch remains in place overnight and is removed in the morning.

The following night, the three-step acne treatment is repeated. Noticeable improvement in the acne lesion is observed within two days of the initial treatment.

Example 3

Three-Step Acne Treatment for Daytime Use

This example provides a three-step acne treatment that is suitable for daytime use. The first step involves topically applying a vasoconstricting composition to the acne lesion to be treated. Suitable vasoconstricting compositions include tetrahydrozoline HCl 0.05%, naphazoline HCl 0.03%, or oxymetazoline HCl 0.025% in an aqueous base containing HPC to increase the viscosity for ease of application. Upon application of the vasoconstricting composition, the redness and swelling of the acne lesion diminishes, making the acne lesion less noticeable. After about 5 minutes, a second step is performed which involves topically applying 5% benzoyl peroxide in an oil-in-water moisturizer base. Next, a water-in-oil moisturizer is applied to minimize evaporation and to help occlude the area.

This treatment is repeated twice daily. Significant healing of the acne lesion is noted after two days.

Example 4

Three-Step Daytime Acne Treatment with Mica and Optional Tinting

This example provides a three-step daytime acne treatment that ingredients for making the acne lesions less noticeable. The first step involves topically applying a vasoconstricting composition to the acne lesion to be treated. Suitable vasoconstricting compositions include tetrahydrozoline HCl 0.05%, naphazoline HCl 0.03%, or oxymetazoline HCl 0.025% in an aqueous base containing HPC to increase the viscosity for ease of application. Upon application of the vasoconstricting composition, the redness and swelling of the acne lesion diminishes, making the acne lesion less noticeable. After about 5 minutes, a second step is performed which involves topically applying 5% benzoyl peroxide in an oil-in-water moisturizer base. Next, a water-in-oil moisturizer is applied to minimize evaporation and to help occlude the area. The water-in-oil moisturizer contains mica to provide cosmetic reduction of the appearance of the acne blemish by interfering with light passing to or from the lesion. Tinting compounds are also present to help conceal the acne lesion, but these compounds are optional.

This treatment is repeated twice daily. Significant healing of the acne lesion is noted after two days.

Example 5

Three-Step Daytime Acne Treatment Plus Cleanser

A skin cleanser to may be used prior to the acne treatment disclosed in Example 3. Generally, the skin cleanser is tailored to be appropriate to the skin type and anatomic location. In this example, the skin cleanser is a decyl sulfate-based skin cleanser that reduces pro-acne components by removing excess skin oils. The skin cleanser may also contain triethanolamine as a penetration enhancer that increase the permeability of skin, thereby enhancing the penetration of the vasoconstrictor and other components of the anti-acne treatment.

Example 6

Three-Step Daytime Spot Treatment with Cleanser and Moisturizer

The anti-acne treatment disclosed in Example 5 can be used in conjunction with a moisturizer to improve skin hydration, suppleness or appearance, or to decrease tendency to form new acne lesions in unaffected areas. This moisturizer optionally may have pigment added for cosmetic benefit. Typically, the cleanser is first applied, followed by the vasoconstrictor and anti-acne agent. Next, the moisturizer is applied to soften the skin while helping to occlude the area. The treatment may be repeated twice daily to obtain noticeable improvement in skin softness and reduction in severity of acne lesions.

Example 7

Three-Step Daytime Acne Treatment and Moisturizer with Sunscreen

The anti-acne treatment disclosed in Example 3 can be used in conjunction with a moisturizer with sunscreen to protect skin from damaging UV rays of the sun and to improve skin hydration, suppleness or appearance, or to decrease tendency to form new acne lesions in unaffected areas. This moisturizer optionally may have pigment added for cosmetic benefit. Typically, a vasoconstricting composition is topical applied and then anti-acne agent. Next, a water-in-oil moisturizer with 7.5% octinoxate (octyl methoxycinnamate) and 3.0% zinc oxide with vitamin C and cucumber extract is applied to provide sun protection. The treatment may be repeated twice daily to obtain noticeable improvement in skin softness and reduction in severity of acne lesions. The moisturizer with sunscreen may be used before sun exposure each morning and throughout the day.

Example 8

Three-Step Daytime Treatment with Mica and Oral Vitamins

The anti-acne treatment described herein can be used in conjunction with nutritional supplements that speed the healing of acne lesions or prevent new acne lesions from forming. The nutritional supplements may be, for example, oral multivitamins. In this particular example, the anti-acne treatment of Example 3 is used in conjunction with zinc and Vitamins C and A, supplements that are well known for their promotion of wound healing. An oral multivitamin containing 10 mg of zinc amino acid chelate, 250 mg of ascorbic acid (Vitamin C), and 5000 IU of beta-carotene (vitamin A) is taken daily in conjunction with the use of the anti-acne treatment of Example 3. Noticeable improvement in the acne lesions is observed after two days.

Example 9

Anti-Acne Treatment for Sensitive Skin

This example provides an anti-acne treatment for sensitive skin. The treatment includes a vasoconstricting composition containing oxymetazoline HCl 0.025% with guava extract and witch hazel in an aqueous base containing acrylate copolymer to increase the viscosity. The vasoconstricting composition is applied topically to an acne lesion to be treated. Upon application, the redness and swelling of the lesion decreases as the blood vessels in the treated region are constricted. For this particular sensitive-skin acne treatment, the anti-acne agent is triclosan, rather than benzoyl peroxide, because about 10% of the population experiences skin allergies when benzoyl peroxide is topically applied. Note, however, that any anti-acne agent not containing benzoyl peroxide may be used. The anti-acne agent is applied about 15 minutes after the initial application of the vasoconstricting composition. Optionally, a third component containing a concealing agent (such as mica) or tinting is applied.

Example 10

Two-Step Day Acne Treatment

This example provides a two-step acne treatment. In the first step, a composition containing oxymetazoline HCl 0.025% with guava extract and witch hazel in an aqueous base is topically applied to the acne lesion to be treated. The viscosity of the composition is increased with HPC to form a creamy or gel-like base for ease of application. The vasoconstrictors applied in the first step decrease the redness and swelling of acne lesion, and help to reduce the diffusion of subsequently applied anti-acne agent from the lesion. In the second step, which is performed about 15 minutes after the first step, a composition that contains 5% benzoyl peroxide (an anti-acne agent) in a base containing water-in-oil moisturizer with 5% grapeseed extract is applied to the acne lesion. The base also contains mica and is optionally tinted to mask the reappearance of the lesion as the vasoconstrictors in the first step wear off.

Example 11

Three-Step Daytime Acne Treatment

This example provides a three step acne treatment. In the first step, a composition containing tetrahydrozoline HCl 0.05%, guava extract, and witch hazel in an aqueous base is applied topically to the acne lesion to be treated. The viscosity of the composition is adjusted with HPC to form a creamy or gel-like base for ease of application. The vasoconstrictors applied in the first step decrease the redness and swelling of acne lesion, and help to reduce the diffusion of subsequently applied anti-acne agent from the lesion. In the second step, which is performed about 15 minutes after the first step, a composition that contains 5% benzoyl peroxide (as an anti-acne agent) in a water-in-oil moisturizer containing 5% grapeseed extract is applied to the acne lesion. To increase flux of the anti-acne agent into the lesion, the third step of the treatment involves subsequently applying a water-in-oil moisturizer that help to prevent evaporation and that provides some degree of occlusion. The water-in-oil moisturizer contains mica and optionally may be tinted to help conceal the acne lesion.

We claim:

1. A method of treating acne, said method comprising:
   applying a vasoconstrictor in a vasoconstricting amount to an acne lesion to achieve a vasoconstrictive effect; and
   subsequently applying an anti-acne agent to said acne lesion wherein the anti-acne agent is administered during the vasoconstrictive elect of said vasoconstrictor.

2. The method according to claim 1, wherein said anti-acne agent is selected from the group consisting of benzoyl peroxide and salicylic acid.

3. The method according to claim 1, wherein the anti-acne agent is applied from 15 seconds to 30 minutes after the application of the vasoconstrictor.

4. The method according to claim 1, wherein the anti-acne agent is applied from 45 seconds to 15 minutes after the application of the vasoconstrictor.

5. The method according to claim 1, wherein the anti-acne agent is applied from one minute to five minutes after the application of the vasoconstrictor.

6. The method according to claim 1, further comprising the step of applying, after application of the anti-acne agent, one or more components selected from the group consisting of a skin lightening therapeutic, a skin cleanser, an astringent, a sun screen and a sealing layer.

7. The method according to claim 6, wherein said vasoconstrictor is selected from the group consisting of tetrahydrozoline HCl 0.5%, naphazoline HCl 0.03%, oxymetazoline HCl 0.025%, guava extract, ellagic acid, caffeine, cypress oil, witch hazel, peppermint extract, chamomile oil, and bugleweed.

8. The method according to claim 6, wherein said skin-lightening therapeutic is selected from the group consisting of albatin, arbutin, bearberry extract, mulberry extract, licorice extract, skull cap, azelaic, ascorbyl glucosamine, magnesium ascorbyl phosphate, ascorbic acid, coltsfoot extract, gallic acid, nutmeg, ramulus mori extract and kojic acid.

9. The method according to claim 6, wherein said sealing layer comprises mica.

* * * * *